United States Patent [19]

Kinsolving et al.

[11] 4,386,105
[45] May 31, 1983

[54] USE OF ALPHA, ALPHA-DIALKYL ADAMANTYLETHYLAMINES TO TREAT MEASLES

[75] Inventors: Clyde R. Kinsolving, Fairport; Ronald C. Griffith, Pittsford, both of N.Y.

[73] Assignee: Pennwalt Corporation, Philadelphia, Pa.

[21] Appl. No.: 350,535

[22] Filed: Feb. 19, 1982

[51] Int. Cl.³ ............................................. A61K 31/13
[52] U.S. Cl. ...................................................... 424/325
[58] Field of Search ......................................... 424/325

[56] References Cited

U.S. PATENT DOCUMENTS 3,592,934   7/1971   Prichard ............................. 424/325

Primary Examiner—Jerome D. Goldberg

[57] ABSTRACT

Warm-blooded animals are treated by administering to the animal a dosage, effective to alleviate the symptoms of measles, of a compound of the formula I or its acid salt:

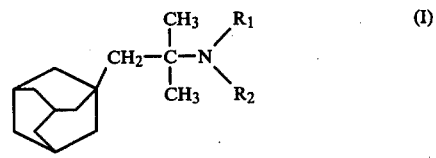

wherein $R_1$ and $R_2$ are selected from the class consisting of hydrogen and —$CH_3$ and at least on pharmaceutically acceptable carrier, wherein the compound is 0.01 to 95% by weight of the composition.

6 Claims, No Drawings

USE OF ALPHA, ALPHA-DIALKYL ADAMANTYLETHYLAMINES TO TREAT MEASLES

BACKGROUND OF THE INVENTION

The invention relates to the use of an antiviral composition for treating measles in warm blooded animals and more particularly to the use of antiviral compositions containing alpha, alpha-dialkylethylamine derivatives of adamantane and at least one pharmaceutically acceptable carrier for the treatment of warm blooded animals infected with measles.

Measles is a highly contagious viral infection involving primarily the respiratory track and reticuleondothelial tissues. It is also called rubeola. A prodrome of three to five days duration begins about eight days after inhalation of the virus in droplets derived from a person in the prodromal or early eruptive phase of the infection. Coryza, cervical lymphadenitis, palpebral, conjunctivitis, protophobia, myalgia, malaise, and a harassing cough with steadily mounting fever precedes the skin eruption. The skin becomes covered with red papules that appear behind the ears and on the face before spreading rapidly down the trunk and onto the arms and legs. The papules are discrete but gradually become more confluent. The lesions flatten, turn brown, and slowly desquamate on about the sixth day, when the temperature has returned to normal. It may be complicated by bacteria, by pneumonia, by otitis media, and by a demyelinating encephalitis. Fatalities are due to the severity of measles itself, or to the bacterial or immunological complications.

No prior art is known which discloses the use of alpha, alpha-dialkyl adamantylethylamines for the treatment of measles.

SUMMARY OF THE INVENTION

This invention is directed to a method for treating measles in warm blooded animals comprising administering to the animals a dosage effective to alleviate the symptoms of measles in warm blooded animals of (i) a compound of the formula I or its acid salt:

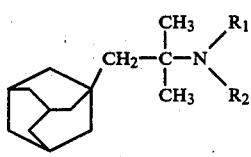

(I)

wherein $R_1$ and $R_2$ are selected from the class consisting of hydrogen and methyl (preferably hydrogen), and (ii) at least one pharmaceutically acceptable carrier, wherein the compound is from about 0.01 to about 95% by weight of the composition. The identity of the acid forming the salt of the amines is not critical. The hydrochloride of the amine is preferred, but any pharmaceutically acceptable inorganic or organic acid such as the sulfate, acetate, nitrate, or the like may be used.

DETAILED DESCRIPTION OF THE INVENTION

The adamantane drug (I) of this invention can be administered in the antiviral treatment according to this invention, either before or after the infection sets in, in a dosage form of the drug for oral or parenteral application (the preferred application form is oral). The dosage form may be a solution, suspension, tablet, or capsule formulation (preferably capsule). The dosage administered will be dependent upon the virus (i.e., Measles) being treated, the weight of the recipient, the frequency of treatment, and the effect desired. Generally in a man, a daily internal dosage of active ingredient compound (I) will be from about 10 to 500 milligrams although lower and higher amounts can be used. The active ingredient, the drug, can be employed in useful compositions according to the present invention in such dosage forms as solution, suspension, semisolid, and solid forms. These dosage forms preferably deliver from about 1 mg to 500 mg of active ingredient, with the range from 10 mg to about 200 mg being most preferred. In these dosage forms the antiviral composition will contain at least one non-toxic pharmaceutically acceptable carrier for the active ingredient. Examples of the non-toxic carriers or adjuvants are viscosity enhancers such as celluloses (e.g., methylcellulose, ethylcellulose, and carboxy methylcellulose) tragacanth, glyceryl monostearate, and stearic acid; pH modifiers such as dibasic sodium phosphate, citric acid, and sodium hydroxide; preservatives such as methyl paraben, propyl paraben, benzoic acid, and benzyl alcohol; sweeteners such as saccharin, sorbitol (D-glucitol), and mannitol; stability enhancers such as sodium bisulfite and ascorbic acid; coloring agents such as food, drug and cosmetic (FD&C) and drug and cosmetic (D&C) colors certified by the Food and Drug Administration (FDA); solvents such as water, alcohol (e.g., ethyl alcohol (for internal use) and propylene glycol; suspending agents such as celluloses (e.g., methylcellulose, ethylcellulose and carboxy methylcellulose), acacia, and tragacanth; granulating agents such as acacia, sucrose, and polyvinylpyrrolidone (PVP); coating agents such as celluloses (e.g., ethylcellulose and propylcellulose) and PVP; disintegration/dissolution modifiers such as starch (e.g., corn starch, rice starch and potato starch) and polysorbate 80 (polyoxyethylene (20) sorbitan monooleate); excipients such as lactose, starch, and cellulose; ion exchange agents such as XE-69 and IR 120 (sulfonic acid cation resins (styrene divinyl benzene)) and IRP 58 (a phenolic polyamine anion exchange resin); emulsifying agents such as glyceryl stearate (self emulsifying), sorbitan stearate, decyloleate, and polysorbate 60.

Typical embodiments of the pharmaceutical composition of this invention are: (all percentages are by weight of composition)

| | |
|---|---|
| 1. Tablet: | |
| drug | 100 mg |
| microcrystalline cellulose | 100 mg |
| magnesium stearate | 5 mg |
| 2. Capsule: | |
| drug | 100 mg |
| lactose | 100 mg |
| starch | 5 mg |
| magnesium | 2 mg |
| 3. Oral Solution: | |
| drug | 2 g |
| sorbitol (D-glucitol) solution 70% | 50 ml |
| citrus flavor | 5 ml |
| citric acid | 1 g |
| distilled water, quantity sufficient to make (q.s. ad) | 100 ml |
| 4. Parenteral Solution: | |
| drug | 2.5 g |
| benzyl alcohol | 0.1 g |
| sterile distilled water, q.s. ad | 100 ml |

-continued

| | |
|---|---|
| 5. Oral Resinated Suspension (sustained release): | |
| drug resinate | 10% |
| (drug content of resin is 15%) | |
| keltrol (xanthan gum) | 10% |
| saccharin | 0.5% |
| flavor | 0.2% |
| sorbitol 70% solution | 50% |
| methylparaben | 0.5% |
| water, q.s. ad | 100% |
| 6. Oral Resinated Capsule (sustained release): | |
| drug resinate | 200 mg |
| (drug content of resin is 50%) | |
| lactose | 100 mg |
| magnesium stearate | 5 mg |

Note that "drug" in each of the above examples is an alpha, alpha-dimethyl adamantylethylamine of the instant invention.

EXAMPLES 1 & 2

The hydrochloride salt of the compound of formula I wherein $R_1$ and $R_2$ are hydrogen (called compound A) was tested for its antiviral activity against measles using a method that was developed by Sidwell[1,2]. Green Monkey kidney tissue cells were grown in micro-culture plates (micro-Petri dishes) in sets of 12 duplicates. These sets of tissue culture plates were inoculated (except the control set) with the measles virus and different concentrations of the drug were added to the wells. Then, these plates were observed for several days and scored by the same person who equated the severity of the destruction of the cells with a numbering system. These plates were rated according to the percentage of cells that were destroyed; this is referred to as the cytopathogenic effect (CPE). Hence, the lower the CPE, the better the protection.

1. L. B. Allen, C. Hintz, S. M. Wolf, J. H. Huffmann, R. K. Robbins and R. W. Sidwell H. Infect. Dis., 133: A178–A183, (1976)
2. L. B. Allen, S. M. Wolf, C. J. Hintz, J. H. Huffman, and R. W. Sidwell, Ann. N.Y. Acad. Sci., 284: 247–253, (1977).

Drug Concentrations of 1,000, 320, 100, 32, 10, 3.2, 1.0, 0.32, and 0.1 micrograms per milliliter were used on different sets of plates for testing the various concentrations on the animal tissue cultures. At each of these concentrations the visible cytotoxicity of the inoculated set of tissue culture plates were observed as well as the CPE. The visible cytotoxicity is an observation made to see whether the drug itself at a particular concentration destroys the cells rather than the measles virus. A plus sign (+) in Table 1, infra, indicates that the drug itself is relatively toxic to the tissue cells and is destroying them rather than the measles virus. Two plus signs (++) indicate more toxicity of the drug to the tissue cells at that particular concentration. The minus sign (—) obviously indicates no toxicity of the drug.

The virus rating is a calculation of the toxicity of the drug on the cells with no virus present in relation to the destroying of the cells observed when the virus is present. This virus rating is a complicated statistical average based on the set of 12 tissue culture plates at each concentration. When the virus rating is 0 to 0.4, the drug is inactive; when the rating is between 0.41 and 0.99, the drug is moderately active; and when the rating is above 1.0, the drug is very active. Hence, the higher is the virus rating, the better is the drug. Also, the lower is the CPE, the better is the drug at that concentration.

In the second example, the hydrochloride salt of the compound of formula I wherein $R_1$ and $R_2$ are methyl (compound B) was tested for its antiviral activity against measles using the same method described for compound A.

Comparative tests were also run on a commercial product called VIRAZOLE using the same procedure as described for Example 1 above.

In these experiments, the lowest concentration where a protective effect of the drug was observed is called the minimum inhibitory concentration (MIC); this was found to be at least 10% protection.

The results of these experiments are recorded in Table 1 as follows:

TABLE 1

| Concentration (μg/ml) | A | | B | | Virazole | |
|---|---|---|---|---|---|---|
| | Visible Cytotoxicity | Avg CPE (%) | Visible Cytotoxicity | Avg CPE (%) | Visible Cytotoxicity | Avg CPE (%) |
| 1000 | | | | | + | 0 |
| 320 | | | | | + | 0 |
| 100 | ++ | Tox | + | 12 | — | 0 |
| 32 | ++ | Tox | — | 44 | — | 7 |
| 10 | — | 25 | — | 50 | — | 38 |
| 3.2 | — | 57 | — | 68 | — | 63 |
| 1.0 | — | 63 | — | 75 | — | 75 |
| 0.32 | — | 88 | — | 75 | | |
| 0.1 | — | 100 | — | 78 | | |
| 0 | — | 100 | — | 100 | — | 100 |
| Virus Rating | | 0.7 | | ≧1.0 | | 1.6 |
| MIC (μg/ml) | | 0.32 | | ≦0.1 | | ≦1.0 |

This Table shows that compound A of the present invention showed moderate antiviral activity while compound B showed strong antiviral activity. Virazole also has strong activity as expected.

What is claimed:

1. A method for treating measles virus in warm-blooded animals comprising administering to the animals an effective amount for treating the measles virus of a composition comprising (i) a compound of formula I or its acid salt:

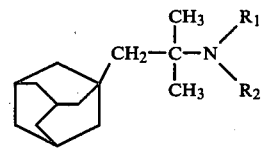
(I)

wherein $R_1$ and $R_2$ are selected from the class consisting of H and —$CH_3$; and (ii) at least one pharmaceutically acceptable carrier, wherein the compound is 0.01 to 95% by weight of the composition.

2. The method of claim 1 wherein the acid salt of the compound is hydrochloride.

3. The method of claim 2 wherein the composition is administered to the warm-blooded animal orally or parenterally.

4. The method of claim 3 wherein the composition is in the form of a capsule, tablet, or solution.

5. The method of claim 1 wherein $R_1$ and $R_2$ are hydrogen.

6. The method of claim 1 wherein $R_1$ and $R_2$ are —$CH_3$.

* * * * *